(12) United States Patent
Gantefort et al.

(10) Patent No.: US 8,877,490 B2
(45) Date of Patent: Nov. 4, 2014

(54) FERMENTER FOR GENERATING BIOGAS FROM PUMPABLE ORGANIC MATERIAL

(76) Inventors: Wilhelm Gantefort, Heiden (DE); Jürgen Beck, Rottenburg (DE)

(*) Notice: Subject to any disclaimer, the term of this patent is extended or adjusted under 35 U.S.C. 154(b) by 1339 days.

(21) Appl. No.: 12/601,500

(22) PCT Filed: May 16, 2008

(86) PCT No.: PCT/EP2008/056005
§ 371 (c)(1),
(2), (4) Date: Apr. 27, 2010

(87) PCT Pub. No.: WO2008/142007
PCT Pub. Date: Nov. 27, 2008

(65) Prior Publication Data
US 2010/0240094 A1    Sep. 23, 2010

(30) Foreign Application Priority Data
May 23, 2007    (DE) .......................... 10 2007 024 378

(51) Int. Cl.
| C12M 1/107 | (2006.01) |
| C12M 1/18 | (2006.01) |
| C12P 5/02 | (2006.01) |
| C12M 1/12 | (2006.01) |
| C12M 1/00 | (2006.01) |

(52) U.S. Cl.
CPC .............. *C12M 23/34* (2013.01); *Y02E 50/343* (2013.01); *C12M 25/18* (2013.01); *C12M 29/00* (2013.01); *C12P 5/023* (2013.01); *C12M 21/04* (2013.01)
USPC ..................... 435/299.1; 435/300.1; 435/167; 210/603

(58) Field of Classification Search
USPC .......... 435/300.1, 299.1; 210/195.3, 603, 617
See application file for complete search history.

(56) References Cited

U.S. PATENT DOCUMENTS

| 3,981,800 | A | * | 9/1976 | Ort ................................ 210/603 |
| 4,532,042 | A | | 7/1985 | Aivasidis |
| 4,627,917 | A | | 12/1986 | Morper |
| 6,342,378 | B1 | * | 1/2002 | Zhang et al. .................. 435/168 |

FOREIGN PATENT DOCUMENTS

| DE | 36 04 415 A1 | 8/1987 |
| DE | 36 08 466 A1 | 9/1987 |
| DE | 37 15 952 A1 | 11/1988 |
| DE | 44 15 017 A1 | 11/1995 |

(Continued)

OTHER PUBLICATIONS

English language machine translation of JP 2005-081238 (Mar. 31, 2005).*

*Primary Examiner* — William H Beisner
(74) *Attorney, Agent, or Firm* — Cesari and McKenna, LLP

(57) ABSTRACT

The invention relates to a fermenter for generating biogas from pumpable organic material with a low content of organic dry matter (oTS), comprising at least one inlet for the pumpable organic material, at least one fixed bed reactor for the pumpable organic material with at least one primary and one secondary section and at least one outlet the remaining fermentation residue. Furthermore, the fermenter can optionally comprises at least one sedimentation chamber for the pumpable organic material, arranged between the primary and secondary sections and at least one recycling section connected to the sedimentation chamber and designed such that specific lighter fractions of the pumpable organic material can be recovered and reintroduced to the rising (primary) section of the fixed bed reactor or a preceding or subsequent conventional fermenter.

21 Claims, 11 Drawing Sheets

(56) References Cited

FOREIGN PATENT DOCUMENTS

| | | | |
|---|---|---|---|
| DE | 4415017 A1 * | 11/1995 | |
| DE | 295 21 085 U1 | 11/1996 | |
| DE | 197 56 485 A1 | 7/1999 | |
| DE | 198 05 580 C1 | 9/1999 | |
| DE | 10 2005 012936 A1 | 10/2006 | |
| EP | 28053 A1 * | 5/1981 | |
| EP | 0 335 825 A | 10/1989 | |
| JP | 2000-033358 | 2/2000 | |
| JP | 2003-326237 | 11/2003 | |
| JP | 2005-081238 | 3/2005 | |
| JP | 2005-125312 | 5/2005 | |
| JP | 2005-144280 | 6/2005 | |
| JP | 2007-098369 | 4/2007 | |
| WO | WO 2005/113469 | 12/2005 | |
| WO | 2007/054193 | 5/2007 | |

\* cited by examiner

32

33

FERMENTER FOR GENERATING BIOGAS FROM PUMPABLE ORGANIC MATERIAL

CROSS-REFERENCE TO RELATED APPLICATIONS

This application is the National Stage of International Application No. PCT/EP2008/056005, filed on May 16, 2008, which claims the benefit of German Application Serial No. 102007024378.4, filed on May 23, 2007, the contents of both of the foregoing applications are hereby incorporated by reference in their entirety.

The invention relates to a fermenter for generating biogas from pumpable organic material with a low content of organic dry matter (oTS) according to claim 1.

Since the discussion involving renewable energies and their production has become more and more the center of public attention, the interest in fermenters for generating biogas has increased. It is known that such fermenters are used in agricultural holdings as well as municipal sewage plants. In principle these fermenters work in such a way that organic material is stored in a closed container and, by means of microbial activity, the organic carbon compounds contained in the material are converted to methane gas, which is extracted and used for heat and/or power generation. The energy thus obtained is almost $CO_2$ neutral because the carbon dioxide released during combustion has been previously withdrawn from the atmosphere through plant photosynthesis.

Subsequently the discussion will first of all focus on the fermentation process, which takes place in the absence of oxygen, in order to produce biogas. The entire fermentation process can be divided in several phases. In the first phase the carbohydrates, through optional and obligatory microorganisms, fats and proteins contained in the substrate to be fermented are broken down into low-molecular hydrocarbon compounds ($C_1$-$C_5$ body). In the process, carbohydrates are successively decomposed to propionic acid or butyric acid or butanol; by way of β oxidation, fatty acids are gradually broken down into $C_2$ units which are released as acetic acid; and amino acids are decomposed according to the Stickland reaction into acetic acid, ammonia and $CO_2$.

These intermediate products, in turn, are decomposed into the methanogenic substrates acetic acid ($CH_3COOH$), hydrogen ($H_2$), carbonic acid ($H_2CO_3$), formic acid (HCOOH) and methanol ($CH_3OH$). Again, by obligatory anaerobic, methane-producing (methanogenic) bacteria of the genera *methanobacterium, methanosarcina* and *methanospirillum*, these methanogenic substrates are decomposed into methane, carbon dioxide and water in the following reaction:

$$CH_3COO^- + H^+ \text{---} > CH_4 + CO_2 \quad 1)$$

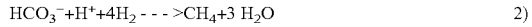
$$HCO_3^- + H^+ + 4H_2 \text{---} > CH_4 + 3\,H_2O \quad 2)$$

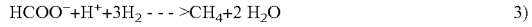
$$HCOO^- + H^+ + 3H_2 \text{---} > CH_4 + 2\,H_2O \quad 3)$$

$$CH_3OH + H_2 \text{---} > CH_4 + H_2O \quad 4)$$

The $HCO_3$ mentioned in reaction 2) is generated by being dissolved from water according to the following equation:

$$H_2O + CO_2 \text{---} > HCO_3^- + H^+. \quad 5)$$

More than 70% of the methane is generated through the splitting of acetic acid, i.e., through reaction 1. Since the biogas fermentation involves a mixing process, in which different microorganisms are active in the various phases, the different requirements of all microorganisms must be taken into account in order to achieve the highest possible yield.

However, the decisive factor is the conditions required for the activity of the methanogenic bacteria. Because of their obligatory anaerobian characteristics, these bacteria require a strictly anoxic environment. Moreover, they prefer a slightly alkaline pH value.

DE 197 564 85 discloses a digester with a stirring unit for use in agricultural biogas plants and municipal sewage plants. This tank comprises a round floor space, a filling nozzle and a stirring unit which has a drive shaft and which is mounted at circumference of the tank. The stirring unit is housed in a pipe which is mounted below the filling nozzle. Preferably, the pipe runs in vertical direction. The content of the fermentation tank is tempered by means of wall heating. The substrate to be fermented is poured into the fermentation tank via a filling nozzle located at a relatively high spot of the tank. By means of an outlet located closer to the bottom, fermented material situated in the lower area of the tank is pumped out and stored in a fermenter.

The substrates that can be used in such a fermenter must have a relatively high proportion of organic dry matter (oTS). For example, energy crops, such as corn or wheat have an oTS proportion of more than 60 percent by weight. With such energy crops it is possible to achieve high biogas yields with a relatively small fermenter volume since maximum volume loads can be obtained with these crops.

The parameter "volume load" is a measurement for the biological load of a fermenter. It is intended to use for a conventional biogas plant a volume load of between 2 and 5 kg oTS/m³ per day. A volume load of 2 kg oTs/m³ per day is considered to be light load. A volume load of more than 5 kg oTs/m³ per day is described as high load.

However, conventional biogas fermenters are only suitable for substrates with high oTS proportions, i.e., especially substrates from renewable resources (NaWaRo), in particular from energy crops such as, grain, silage corn or mangold.

Substrates with low oTS proportions, as, for example, liquid manure, fermentation residues, brewer grains (residues from alcohol fermentation, especially bioethanol production), sewage sludge or highly contaminated sewage water from the food processing industry are not suitable for an exclusive use in these fermenters. At best they are suitable to be used as a seed substrate or as part of a mixture with energy crop substrates (i.e., for the purpose of co-fermentation) since the amount of producible biogas per m³ digester capacity is so low that it is almost impossible to recover the energy (heat energy, power to actuate the stirring unit) required for operating the fermenter.

This is due to the fact that because of the low oTS proportion it is impossible to achieve high volume loads with these substrates without risking a massive washout of methanogenes.

In addition conventional fermenters are permanently dealing with the problem of having to concentrate propionic acid which, starting at a specific concentration, have bacteriostatic and fungistatic effects. This problem occurs if during high volume load the formation of volatile fatty acids, as, for example, acetic acid, is slower than their decomposition by means of methanogenes. In conventional fermenters, their concentration is permanently reduced through washout and the reduplication of methanogenic bacteria, which takes 10-14 days, occurs at an extremely slow pace compared with the acidifiers, which take 0.5-2 hours. Consequently, the content in conventional fermenter systems acidifies very quickly (stopped methanogenesis) and propionic acid is formed.

Liquid manure forms an anoxic system with a relatively high pH value. It is therefore extremely suitable for providing the conditions required for methanogenic bacteria in a biogas fermenter. Nevertheless, it takes longer for microorganisms to metabolize the organic dry substance of liquid manure than it does to metabolize the organic dry substance of energy crops. Consequently, it is required to leave the liquid manure longer in the fermenter.

For example, a cattle farm with 400 LUs (livestock units, 1 LU corresponds to 500 kg live weight) produces approximately 20 m$^3$ of liquid manure per day to be treated. With a storage period of 50 days and a customarily design a fermenter with a tank capacity of 1,000 m$^3$ would be required.

Liquid manure of cattle comprises an average oTS proportion of approximately 6 percent by weight. If a yield of 500 m$^3$ biogas per ton oTS is anticipated, according to the following equations:

$$20 \text{ m}^3 \text{ liquid manure} * 0.6 \text{ percent by weight} = 1.2 \text{ tons oTS} \quad \text{(equation 1)}$$

$$1.2 \text{ tons oTS} * 500 = 600 \text{ m}^3 \quad \text{(equation 2)}$$

the above-mentioned example would result in a biogas yield of 600 m$^3$/day.

However, if a fermenter of the same dimensions is loaded with energy crops, it is possible to run a higher volume load because of the higher oTS proportion, which would result in considerably improved reactor-specific biogas yields.

Since a biogas fermenter involves considerable power consumption (especially for the stirring unit and the heating system), it is inefficient to use in a conventional biogas fermenter exclusively or primarily materials with low contents of organic dry substances (oTS), such as liquid manure.

Nevertheless, in agricultural holdings there is considerable demand for a biological treatment of farm-produced fertilizer (animal waste and fecal matter), in particular liquid manure.

The application of liquid manure on farmland is subject to stringent requirements by law. For example, only sanitized liquid manure may be applied to pastures of dairy cattle. The sanitization is performed by means of a chemical (with NaOH) or thermal process and involves in either case considerable expenses.

It could certainly be considered to perform such sanitization in a biogas fermenter which is operated in the hemophilic range (>55° C.). However, as indicated above, conventional fermenters are not suitable for an effective large-scale treatment of liquid manure.

Moreover, after applying sanitized as well as untreated liquid manure to a field, meadow or pasture land, a generation of climate-damaging gases is promoted. Not only is the generation of carbon dioxide ($CO_2$) promoted but especially the generation of methane gas ($CH_4$), ammoniac ($NH_3$) and nitrous oxide ($N_2O$), which escape into the atmosphere, thus promoting the greenhouse effect.

It is therefore the objective of the invention to provide a fermenter as well as a method of producing biogas which allows for an economic fermentation of organic material with a low content of organic dry substance (oTS).

However, this fermenter should also be able to produce highly efficient and stable methane with highly concentrated substrate mixtures at a high volume load (>5 kg oTS/m$^3$ digester×d). Among other things, this is possible because of the fixed biomass and the recovery of active biomass (preferably methanogenes) for recovery and inoculation in the mixing area.

The invention has the further objective of providing a fermenter as well as a method for an economic treatment and sanitization of liquid manure.

This objective is achieved by means of the characteristics of Claim 1. The sub-claims involve preferred embodiments. It must be considered that all area specifications mentioned include the respective limit values.

Accordingly, a fermenter is designed to generate biogas from pumpable organic material with a low content of organic dry substance (oTS). It comprises a) at least an inlet for the pumpable organic material,
b) at least a fixed bed reactor for the pumpable organic material with at least one primary and one secondary section, as well as
c) at least one outlet for the remaining fermentation residue.

Figure 1:
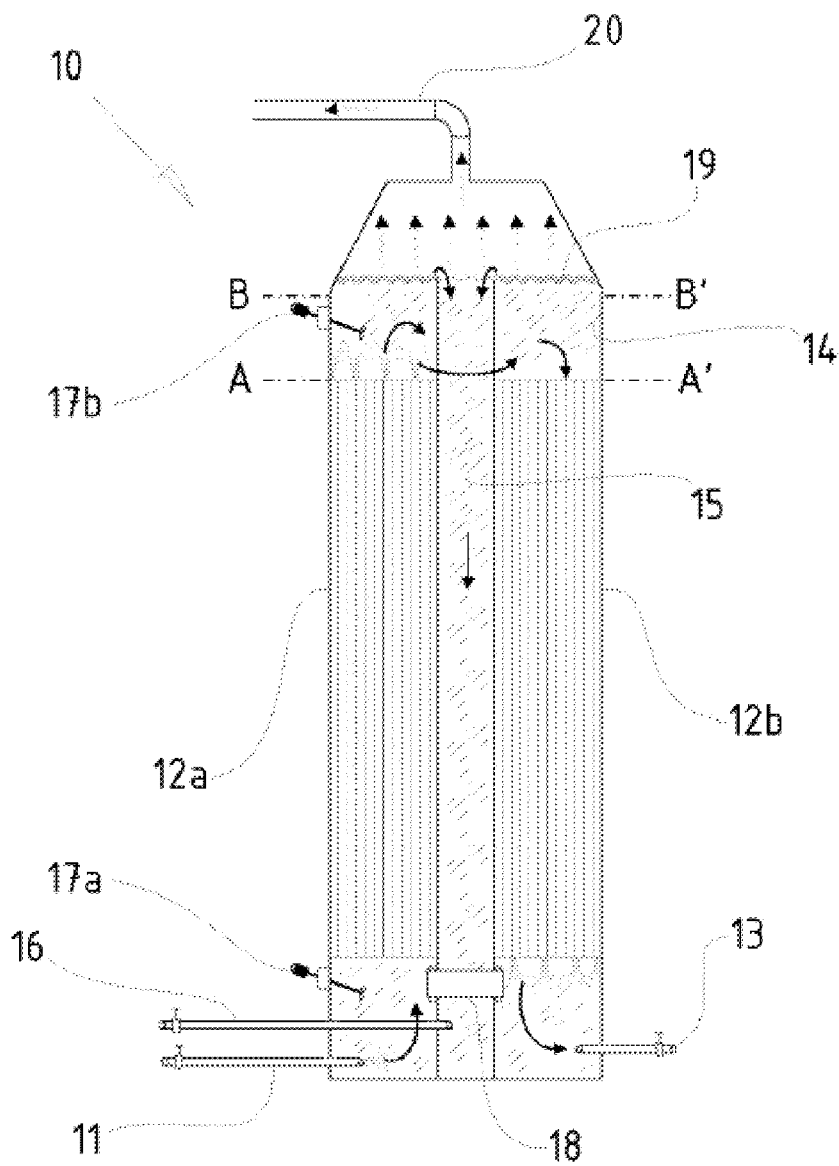
FIG. 1 shows a longitudinal exemplification of an embodiment of an invention-based fermenter.

The definition "organic material with a low content of organic dry substance" should basically involve such materials that comprise an oTS proportion of less than 50 percent by weight, preferred less than 25 percent by weight, and especially preferred less than 10 percent by weight.

Such material comprises, for example, liquid manure, i.e., a farm-produced fertilizer (which mostly has an oTS proportion of less than 10 percent by weight) consisting of animal waste, urine, litter, feed remains and drinking trough water leakages.

For example, a compatible material would also be the fermentation residue from a conventional stirred-tank biogas plant, but also materials such as brewer grains (residues from alcohol fermentation, especially bioethanol production), sewage sludge or highly contaminated sewage water from the food processing industry. The above-mentioned definition involves also liquid manure or fermentation residues mixed with substrates from renewable resources (NaWaRO).

A number of advantages can be achieved by using a fixed bed reactor. For example, a fixed bed reactor does not require its own stirring unit because it is possible to direct the flow of material inside the reactor. This can be compared with a parallel-aligned intestinal tract which is covered inside and outside with intestinal villi and provides a large microbial populating surface, resulting in a flow of substrates directed upward or downward depending on the respective processing stage.

Instead, it is possible to use an energy-efficient pump, in particular a double piston pump. By default, the conventionally used stirring units have a power consumption of approximately 18 kW. By using a double piston pump it is possible to achieve energy savings of up to 90 percent. This considerably increases the efficiency of the invention-based fermenter.

By means of a directed flow of material (forced passage), especially the short-circuit currents, which are unavoidable in fermenter with a stirring unit, are prevented. These short-circuit currents interfere with an effective sanitization of the fermenting material as well as with an ideal fermentation. Both points will subsequently be discussed in more detail.

The provided fixed bed reactor supplies also a colonization substrate for methane-producing micro-organisms. In this way, contrary to a fermenter with a stirring unit, it is possible to achieve a layered formation of microbiocoenosis.

This allows the second metabolic pathway of methane production to take place on a large scale and even to be optimized. To this end microbes interact in small spaces so efficiently that $H^+$ and $CO_2$ (as $HCO_3$) can be synthesized to $CH_4$ (reaction 2). This reduces the $CO_2$ content in biogas and respectively increases the $CH_4$ content. This serves to improve the quality and increase efficiency.

This is very important because specific bacteria and microorganisms required for biogas production are not allowed to come in contact with the substrate to be fermented. In a fermenter with a stirring unit, in which the microorganisms are not provided with a colonization substrate, such layering cannot be obtained, resulting in a considerably lower biogas yield.

In the biogas synthesis there is a differentiation especially of the steps of acetogenesis and methanogenesis which are caused by different microorganisms. During the process of acetogenesis the lower fatty acids and carboxylic acids, as well as the lower alcohols are converted through acetogenic microorganisms primarily to acetic acid, or its dissolved salt, the acetate. During the process of methanogenesis, which is obligatory anaerobic, the acetic acid is converted through respective acetoclastic methanogenes to methane and carbon dioxide, as well as hydrogen. The respective microorganisms form a symbiosis, i.e., one group of microorganisms uses as substrate of reactant the metabolic products of the other microorganisms.

Especially the metabolic pathway $$HCO_3^- + H^+ + 4H_2 \text{ - - - } > CH_4 + 3H_2O \quad\quad 2$$

can hardly be performed in conventional fermenters since the $H^+$ ion transmission has to take place in the range of a nanosecond. This involves an immobilization of the symbiotic microbes in order to guarantee the close proximity required.

Moreover, the microorganisms adapt faster in the fixed bed reactor and, by recovering the active (methanogenic) biomass, the fermenter "starts to operate" faster (due to permanent reinoculation). As a result, the microorganisms are able to break down better and faster the propionic acid mentioned, or it cannot even be generated.

According to the invention, it is preferred that the fermenter also comprises
a) at least one sedimentation chamber for the pumpable material, which chamber is located between the primary and secondary section of the fixed bed reactor, as well as
b) at least one recycling section which is connected to the sedimentation chamber and which is designed in such a way that specific lighter fractions of the pumpable organic material can be recovered and, if required, can be re-supplied to the rising (primary) section of the fixed bed reactor.

In the case of two separate process parts, the sedimentation chamber can be located in each head piece. By means of this first installation of a recycling section specific lighter fractions of the pumpable organic material are recovered and can be re-supplied to the rising (primary) section of the fixed bed reactor.

On the one hand, these specific lighter fractions involve specific lighter organic fractions, as, for example, volatile fatty acids or fibrous biomass, in which the methanogenes and their generated gases are caught and start rising because of the methane and carbon dioxide releases. In conventional fermenters with stirring units these fractions form a floating layer and thus evade the fermentation process. This floating layer could also involve the danger that excess pressure forms in the substrate if the microbial gas bubbles can no longer be dissolved from the floating layer, for example, if the stirring unit fails.

Incidentally some of the volatile fatty acids easily transform into the gaseous phase and are thus permanently excluded from the fermentation process.

The specific lighter organic fractions contain also microorganisms (so-called "active biomass") which have been dissolved from the substrate of the fixed bed reactor and, without a recycling section, would be discharged with the fermentation residue from the fermenter. This involves also a continuous loss of micronutrients which have to be supplemented in conventional fermenters with a stirring unit. This, in turn, results in additional expenses and an additional introduction of heavy metal. Consequently, in conventional biogas fermenters the density of biogas-producing microorganisms is continuously reduced which results in the fact that these fermenters are basically operated with a microorganism density that is too low to achieve an ideal biogas yield. The invention-based recycling section allows these microorganisms to be recovered and re-supplied into the fermenter. As a result, the invention-based fermenter has a considerably higher density of microorganisms than a conventional fermenter and a considerably improved supply of micronutrients, which are circulated via the active biomass.

This provides the possibility to recover the active biomass (which, in equipments according to prior art, is stored together with the fermented material in a fermentation residue storage tank and remains there unused) and re-supply it to the fermentation process. This considerably increases the yield in conventional fermenters. Moreover, by re-supplying the active biomass into the digester, the period for optimizing the plant during a first operation is considerably reduced. In principle it takes a certain amount of time to optimize the operation of a biogas plant. This is due to the fact that first of all a stable flora of microorganisms has to be established in the plant. By means of the possibility to recover the microorganisms that are still present in the fermented material extracted from the digester, the period of building a stable and highly efficient micro flora is considerably reduced. As a result the maximum yield is achieved in a considerably shorter period of time.

The possibility of recovering the active biomass involves another advantage: The fermentation process is accelerated because it is possible to maintain in the digester a considerably higher density of active microorganisms. In this way, the flow capacity of the fermenter can be increased. This results in the fact that the invention-based fermenter can tolerate a considerably higher volume load.

This effect is also achieved if the invention-based fermenter is used in combination with a conventional stirred-tank fermenter, if the recovered active biomass is re-supplied to the stirred-tank fermenter (so-called "repowering," see below).

What is more the invention-based fermenter makes it possible to dispense the addition of micronutrients, which is often required in conventional stirred-tank fermenters, because of re-supplying the active biomass which contains the micronutrients.

In conventional stirred-tank fermenters it is also necessary to thoroughly mix the content of the fermenter. The stirring process continuously disrupts the symbioses of the different microorganisms, especially the methane bacteria. In this way, it is not possible to achieve longer lasting process stability at high proficiency levels. Here, the decaying substrate has to serve the microorganisms simultaneously as nutrient substrate and as surface for symbiotic colonization. Therefore the substrate must provide a certain minimum structure. However, in the invention-based fermenter extremely stable symbioses of permanently established methane bacteria are formed. As a result, methanation can take place in an ideal manner even if the lightly structured substrates are readily biodegradable.

Bacteria producing free hydrogen and bacteria utilizing hydrogen should be permanently established for ideal symbiosis. In the invention-based fermenter, the populating areas of the fixed bed reactors provide the ideal conditions for producing methane gas.

The remaining regions of the invention-based fermenter provide ideal conditions for the development of ideal biological processes which are especially not disrupted by stirring processes.

For optimum fermentation, the microorganisms require not only organic acids, but also $CO_2$.

In the supply area of the organic material an increased amount of $CO_2$ is formed which flows in an optimum way through the higher, rising sections of the fixed bed reactor. Consequently, the methane bacteria are provided with a sufficient amount of $CO_2$ for methanation. This results in optimum biological stability.

Therefore, the biogas in the invention-based fermenter has been improved, especially regarding materials with a low oTS proportion. The improved yield is based on additional decomposition of the oTS, especially by improving the decomposition of equivalents of acetic acid in the production of the plant, and by reusing the recovered bacteria. This is done by utilizing the metabolic activities and/or, if dead, by using the biomass.

Overall, the invention-based fermenter has the following additional advantages:
- The storage period of the substrates (in particular liquid manure) is reduced from 50 to 10 days, thus increasing flow capacity.
- The calculated heat demand is reduced to 20 percent (in practice, the intrinsic process heat is usually already sufficient, i.e., external heat supply is not required).
- Compared with a conventional stirred-tank fermenter, the capacity of the fermenter can be reduced from 1,000 m³ to 200 m³, which reduces building and investment costs.

In a preferred embodiment of the invention-based fermenter, the primary section of the fixed bed reactor has been designed as a rising section and the secondary section of the fixed bed reactor as a descending section.

In this way, it is possible for the first time to allow for and optimize on a large scale the second metabolic pathway of methane production. For this purpose microbes interact so efficiently that $H^+$ and $HCO_3$ can be synthesized to $CH_4$ (see reaction 2). As a result the $CO_2$ content in biogas is reduced and the $CH_4$ content is correspondingly increased. This serves the purpose of improving the quality and increasing efficiency. Because of the finely distributed $CO_2$ bubbles and their large specific surface, there is the chance in the rising section that the methanogenes can enter in intensive contact this second path of methanogenesis which is considerably more difficult to realize.

However, the invention-based fermenter is also able to produce highly efficient and stable biogas with highly concentrated substrate mixtures at high volume load (>5 kg oTS/ m³ digester×d). This is possible because of the fixed biomass and recovery of active biomass (preferably methanogenes) for re-supply and inoculation in the mixing area. The combination of the separate sections of fermentation with upflow and downflow simulate the small intestine and large intestine function, thus transferring the principles of bionics into chemical engineering.

In this analogy, upstream long-term hydrolysis, or the mixing area, accepts the stomach function, as it were, which causes an efficient acidification of the input substrate.

In addition, $CO_2$ can be supplied from external sources in order to intensify the reactions in the rising section. The latter can come from external sources, particularly from an upstream long-term hydrolytic reactor.

Moreover it is preferably intended that the fixed bed reactor comprises a material which provides a large populating surface for microorganisms.

For example, this involves materials with a structured surface and/or an inner surface. This can comprise, for example, materials with a structured plastic surface, but also granules of lava, ceramic pellets, textile, metal or wooden structures and the like.

This allows for a large populating surface and, consequently, high density and stability of the biogas-producing symbiotic microorganism colonies.

It is especially preferred to provide the fixed bed reactor with a material that allows for a formation of basically longitudinal channels.

The term "basically longitudinal channels" involves materials that are suitable to provide the substrate to be fermented in the rising (primary) section and/or the descending (secondary) section of the fermenter with a consistent flow direction. This is also advantageous in that it prevents short-circuit currents. This is subsequently discussed in more detail. Possible materials to be used for this purpose involve, for example, vertical pipes consisting of ceramics, clay, earthenware, metal, wood or plastic material, or vertical rods, boards, honeycombs, ropes, cords or strings.

It is especially preferred if the fixed bed reactor comprises a material that provides a large surface for microbial colonization and allows for the formation of basically longitudinal channels.

Here it has been especially considered to use plastic pipes with an enlarged surface, as, for example, the known flexible drain pipes used in underground construction with a diameter of between 50 and 400 mm. They have a corrugated wall structure which makes it possible that microorganisms populate the external as well as internal surfaces of the pipes.

Said pipes are especially advantageous because they ensure particularly in the rising section of the fixed bed reactor that the rising gas bubbles (especially $CO_2$) do not exceed a specific size. In conventional fermenters the rising gas bubbles increase strongly disproportionately due to a reduction of hydrostatic pressure as well as due to admission of further gas bubbles. On the one hand, this decreases their relative surface. On the other hand, it considerably increases their rising speed. Both situations are responsible that the rising $CO_2$ can no longer metabolize and can no longer be transformed into methane gas according to reaction 2). Equipment with pipes or similar hollow parts restricts the increase in body size of the bubbles. Through compartmentalization of the substrate flow takes care that rising $CO_2$ is further metabolized in parallel and, consequently, stabilized structures.

Preferably, each upper and lower end of the fixed bed reactor is provided with a retaining device for the plastic pipes which fixes the best possible distance of the pipes to one another and which does not restrict the pipe passages, but rather prevents such restrictions.

For example, this retaining device can consist of stainless steel pipe sections ("sleeves") which are arranged in a surface area and welded, inserted, screwed or riveted with angle brackets.

Preferably, plastic pipes are used which have an inside diameter of 100-300 mm and a distance to one another of between 50-300 mm. It is especially preferred if the inside diameter amounts to 200 mm and the distance of the pipes to one another amounts to 100 mm.

Arranging at least one fixed bed reactor with at least one rising (primary) and one descending (secondary) section prevents especially short-circuit currents from forming. This is especially important because only such a forced passage can guarantee that the material can be fermented (i.e., mineralized) in the best-possible manner and that the fermenting material is completely sanitized.

Because of legal regulations, the latter is required for materials which contain animal waste or which were produced by animal waste before applying them to specific farmland areas, such as dairy cattle pastures. The same applies to applications in water protection areas.

The invention-based arrangement guarantees that the entire material to be fermented passes through the entire fixed bed reactor. In the thermophilic range (i.e., at temperatures of more than 55° C.), a storage period of 24 hours is sufficient for adequate sanitization.

Sanitization deactivates mesophilic germs (pathogenic, optional pathogenic and nonpathogenic), as, for example, Coliform bacteria, salmonellae, brucellosis pathogens and the like. The microorganisms required for biogas synthesis are consistently thermophilic. As a result they survive the specified temperatures without damage. At the same time they develop maximum activity. Moreover, because of the excellent colonization substrate they remain in the fermenter and are not flushed out with the fermentation residue, i.e., they are not applied on a dairy cattle pasture.

Under certain conditions the heat generated during biogas synthesis is sufficient to adjust the thermophilic conditions in the fermenter, i.e., it is not required to provide an extreme heat input, which, in turn, results in considerable energy savings.

In an especially preferred embodiment, the invention-based recycling section is connected to the sedimentation chamber by means of an overflow edge. This recycling section is designed in such a way that specific lighter fractions of the pumpable organic material are recovered and can be re-supplied to the rising (primary) section of the fixed bed reactor. These specific lighter fractions contain in particular a large portion of methanogenic microorganisms which would otherwise be flushed out of the fermenter, thus being lost for fermentation.

This effect is supported in that said methanogenic microorganisms colonize on the surfaces of the fixed bed. In this way, they cannot be flushed out.

Alternatively this recovered active material can be re-supplied also in the context of the "repowering process" to the conventional fermenter to be intensified. There it is going to increase the concentration of methanogenes and to allow for an increase of flow capacity or performance.

It can also be arranged that the recycling section is connected to the sedimentation chamber by means of peripheral boreholes or screening devices. However, without using inventive step, an expert can derive from this information other possibilities of how to form the above-mentioned connection between the recycling section and the sedimentation chamber.

In addition it can be arranged that a scraper is provided at the overflow edge of the bore holes or screening devices. This scraper prevents the boreholes or screening devices from being obstructed and avoids that a floating layer forms at the overflow edge. The recovered material, which is described in some embodiments of the present invention as "seed sludge," can be supplied to the organic material to be fermented and to be re-supplied to the fermenter. Preferably, a metering unit has been provided for this purpose, which is preferably, controlled electronically of by means of a microprocessor. In this way, the concentration of the methanogenic microorganisms is permanently increased, which, in turn, proves to be a benefit for the biogas yield and quality.

In principle, by means of the design of the recycling section, it is possible to adjust the volume ratio between the material re-supplied to the fermenter and the material retained in the recycling section. For example, this can take place by specifically selecting the height of a designated overflow edge in relation to the upper edge of the rising section of the fixed bed reactor. It can also take place by specifically selecting the size and/or density of the peripheral boreholes. However, without using inventive step, an expert can derive from this information other possibilities of how to perform the above-mentioned volume ratio adjustment.

Preferably, it has been arranged that the volume ratio between the material re-supplied to the fermenter and the material retained in the recycling section ranges between 1:0.9-2:0.1. It is especially preferred if the volume ratio amounts to 2:1. "Reinoculation with the retained material should be so large that problem-free fermentation is guaranteed and no partial acidification takes place. It is easy for the expert to reproduce these processes with the appropriate methods (pH meter, NIRS, GC sampling).

It is also preferred that the recycling section consists of one, if required, several basically vertical pipe-shaped elements.

Moreover, preferably, the recycling section is located between the rising (primary) and the descending (secondary) section of at least one fixed bed reactor.

This embodiment has a number of advantages. For example, the biogas still generated in the recycling section can be collected by the same gas collection device which collects the gas generated in the sections of the fixed bed reactor or reactors. Furthermore, in this way, it is easy to bring the recycling section to the same temperature that is in the fixed bed reactor or reactors. That way the position of the recycling section is also ideal for recovering the specific lighter fractions because it is located in the center of the sedimentation chamber; especially if the upper edge of the recycling section forms an overflow edge. Incidentally the equipment has also manufacturing advantages which will subsequently be discussed in more detail.

Nevertheless it is also possible and thus within the scope of protection of the claims that the recycling section is not located between the rising (primary) and the descending (secondary) section of at least one fixed bed reactor, but instead, for example, laterally or outside of the actual fermenter.

In an especially preferred embodiment an additional recycling section is located behind the descending (secondary) section of the fixed bed reactor. In this way, the recovery of said substrates and microorganisms is further improved.

Preferably, the fermenter comprises the external form of one or two vertically arranged cylinder(s). To this end it can be arranged that the fermenter or the cylinder (or cylinders) consists of several segments which can be produced in a manufacturing company and assembled to a fermenter on site.

For example, two cylinder halves or several cylinder sections could be provided which are erected on site and welded together or screwed together by means of mounting brackets. Ideally one of the cylinder halves or cylinder sections includes already the recycling section, which also facilitates production and installation and thus reduces costs.

The inventors calculated that such a prefabricated fermenter with a volume of between 200-250 $m^3$ could be built on site within one of two days. In this way, the assembly costs (working hours, equipment, mobile crane) and associated expenses could be considerably reduced. Moreover, the operational activities on site (for example, on a farm) are only insignificantly interrupted. This also guarantees that the fermenter is manufactured according to standard and thus has a high quality standard.

It can also be arranged that the fermenter has a gas collection device which is located at least partially above the fixed bed reactor and/or the recovery device.

For example, this gas collection device can involve a dome or roof construction with a gastight diaphragm located underneath. In such an embodiment it can be especially arranged that the gas collection device also has the function of a gas storage system. In this case the gastight diaphragm hangs loosely above the digester as long as only a small amount of gas has been developed. However, the developing gas pushes the diaphragm upwards and it becomes tight. Then the generated gas can be extracted in a known manner and with known extraction devices.

Basically it can be arranged that the invention-based fermenter comprises also a device to feed the generated biogas into a gas pipeline network. However, it is preferred that the invention-based fermenter is connected to the device which converts the generated biogas into electricity.

To convert the chemical energy contained in the generated gas into electrical energy, the biogas is converted into electricity, for example, in a cogeneration unit (BHKW) which includes a gas engine or a dual fuel engine. To be able to work economically the gas to be burned must be supplied to the gas engine with an initial pressure of approximately 100 mbar. In conventional biogas plants a separate gas pressure blower is required to bring the stored gas to the above-mentioned initial pressure. On the one hand, this blower uses a considerable amount of energy. However, it increases the maintenance requirements and acquisition costs, as well as the control effort of a biogas plant.

It is especially preferred that the fermenter comprises a hydrostatic gas storage system.

The term "hydrostatic gas storage system" involves a gas storage system (which is subsequently described in more detail) in which the supplied gas displaces a previously available liquid (in particular water) with gravity (and thus against the formation of hydrostatic pressure or a water column). With regard to this embodiment reference is made to the drawings.

If the gas storage system is constructed in a way that, when displacing the liquid available in the system, the gas inflow forms a maximum water column of 2,000 mm, it corresponds to a hydrostatic pressure of 200 mbar. At the same time, the pressure of the stored gas is maintained at a level corresponding to the hydrostatic pressure and can be supplied to the gas engine of the BHKW without using its own gas pressure blower. For this purpose it is essential that the biogas generating microorganisms are able to continue to produce biogas even against strong pressure gradients. In the literature pressure gradients of up to 160 bars are described. Consequently, the biogas synthesis is not affected by the described accumulating pressure gradient of 200 mbar, which could possible continue all the way into the fermenter.

Preferably, the pipelines leading to the hydrostatic gas storage system are dimensioned in such a way that they fulfill the requirements for gas safety devices (high pressure and low pressure). For example, an excess generation of gas can escape into the environment through the hydrostatic gas storage system. At the same time the liquid of the gas storage system functions as a flashback protector and eliminates the danger of explosion or fire in the fermenter. A conventional gas storage system is not able to do that. Moreover, with specific dimensions, the pipelines can also be used as an overflow safety device for fermentation substrate that has been fed in excess into the fermenter. This fermentation substrate is drained off through the pipelines and is collected by means of the hydrostatic gas storage system.

Preferably, the gas collection device of the fermenter comprises a conical or frustoconical, paraboloid or hemispherical dome.

It is especially preferred that this dome is arranged on the fermenter in such a way that the tapering region of the dome, which is directed upwards, starts below the overflow edge of the recycling section. In this context, reference is made to the drawings. As a result, the recovery of the active biomass is considerably improved.

Furthermore, it is preferred that no electrical devices have been arranged for the region of the digester, the gas storage system and/or the settling chamber. The digester, the gas storage system and/or the settling chamber can be designed also as Faraday cage. Both methods serve as a fire and explosion prevention. For this purpose the housing of the fermenter as a whole can consist of conducting metal (especially $V_4A$ steel or corrosion-resistant coated steel), or it can consist of a non-metal material provided with a network of metallic conductors, for example, in the form of a wire netting surrounding the housing material.

In a further preferred embodiment, the invention-based fermenter comprises a settling channel located in the base of the digester. In this settling channel organic material, such as sand, lime and stone, etc., can settle and be removed from the fermenter by means of a conveyor screw. Usually between approximately 1-3 percent fermenting material is removed in this way on a daily basis. It is then possible to separate solid matter from the discharged material and to re-supply the liquid components into the digester.

In a further preferred embodiment a heat exchanger has been arranged in the region of the outlet of the fermenter. By means of this heat exchanger the fresh organic material to be fermented can be pre-heated.

In this way it is considerably easier to adjust the mesophilic or thermophilic conditions in the fermenter. At the same time it reduces the energy consumption required. In an ideal case, the intrinsic reaction heat developing during the fermentation process is sufficient to adjust the above-mentioned conditions. Consequently, no additional heat supply from the outside is required.

In some cases, i.e., if the intrinsic reaction heat is not sufficient, the invention-based fermenter has to be tempered. Several heating devices, for example, heat exchangers located in the fermenter, have a surface temperature that is too high for the microorganisms. Consequently, fermenting material coming in contact with the heating device is initially heated to a temperature that is above the preferred temperature range and releases this temperature successively to the surrounding material. In this way, it is possible to adjust the entire digester to the desired temperature. However, the increased temperature causes the microorganisms (especially methanogenic bacteria) colonizing in the region of the heating device or coming in contact with it to die off. This, in turn, reduces the yield.

It is also preferred that the fermenter comprises a temperature control device for the organic material to be fermented that is set in such a way that the temperature of the fermenting material, which is brought into the digester through the inlet, can be adjusted only by heating the organic material to be fermented.

Besides a heating device for the substrate to be fermented, this requires that the digester is equipped with at least one temperature probe and a respective control circuit. This type of temperature control is especially effective because the tempered material brought into the digester is immediately distributed and quickly releases its thermal energy to the surrounding area. Because of the quick heat exchange to the surrounding material, the life processes of the methanogenic bacteria in the fermenter are not affected. Moreover, because of the excellent thermal conductivity and the effective mixing, only an insignificant increase of temperature of the substrate to be fermented is sufficient to control effectively the temperature in the fermenter. Consequently there is no reason to be afraid that the methanogenic bacteria in the fermenter are damaged. Altogether it is possible to heat the fermenting material more evenly and rapidly, which has a positive effect on the process stability. To this end, it can be preferable that the filling device is located between the two stirring units. In this way, the tempered substrate to be fermented is brought into the digester in an especially effective manner and is quickly mixed in with the fermenting material, releasing its temperature very quickly to the surrounding area. This also provides the possibility of pasteurizing or sterilizing the substrate to be fermented before bringing it into the digester. In this way, it can be very quickly colonized with methanogenic bacteria after it has been brought into the digester, which will force fermentation and thus increase the yield. With this type of temperature control it is not necessary to provide the digester with additional heating devices or heat exchangers, preventing the above-mentioned damages. Moreover, with this type of temperature control, it is also not required to provide electric circuits in the digester, which otherwise could involve the danger of explosion and fire.

In addition, according to one of the previous claims, the invention provides a method of producing biogas in a fermenter from pumpable organic material with a low content of organic dry substance (oTS). The method involves the following steps:

a) bringing pumpable organic material into the fermenter by means of an inlet,
b) producing and maintaining an anaerobic environment, a pH value of at least 7 and temperature in a mesophilic to thermophilic range,
c) producing a flow of material of pumpable organic material through the fixed bed reactor as well as the sedimentation chamber of the fermenter,
d) recovering in the recycling section the specific lighter fractions of the pumpable organic material,
e) if possible, re-supplying the recovered material to the fermenter,
f) collecting the generated gas and extracting the fermented fermentation residue continuously and in batches.

At the same time, the pH value can be adjusted with the usual methods known to an expert.

In particular it can be arranged that the flow of material through the fixed bed reactor is produced continuously or in a pulsating manner. Both types can have advantages and disadvantages, especially with regard to the respective substrate used. For example, a pulsating flow of material can be of advantage in order to provide a longer contact time between the substrate to be fermented and the microorganisms. By means of routine tests and without using inventive step, an expert can easily learn suitable flow conditions (speed, pulse intervals, etc., especially with regard to the respective substrate used).

According to the invention, it has also been arranged that the recovered material is pre-incubated with fresh material to be fermented before the fresh material is brought into the fermenter.

It is especially preferred that, for the purpose of full utilization, more biomass from renewable resources, especially energy crops, is supplied to the organic material to be fermented, which organic material has low proportions of organic dry substance (oTS).

The fermentation residues produced with the invention-based fermenter or method comprise a high proportion of mineralized nutrients (N, P, K) and are well suited as fertilizer. Compared with the fermenting substrate, the fermentation residues usually have low viscosity since they contain a lower proportion of residual organic matter. Therefore they can be easier spread and utilized for plant production than, for example, liquid manure. Because of the reduced proportion of organic substances, there is the danger that, after discharging the fermentation residue, there will be a considerably low formation of greenhouse gases, such as, carbon dioxide ($CO_2$), methane gas ($CH_4$), and nitrous oxide ($N_2O$). Moreover, plant seeds possibly contained in the liquid manure, especially weed seeds and fungal spores, are deactivated by the fermentation. Consequently, after being discharged they can no longer germinate. A further advantage of the fermentation residues produced in this way is the fact that they are sanitized if specific process conditions are maintained. Therefore, without further chemical or thermal treatment, they can be applied also to critical surfaces, as, for example, water protection areas or dairy cattle pastures.

Moreover, the liquid manure is highly mineralized, i.e., the plants to be fertilized benefit much more from the nutrients contained. However, if unfermented liquid manure is used for fertilization, an incalculable potential of organically bound nutrients is created in the soil. During natural mineralization phases, this can have a considerable impact on the groundwater if the vegetation is not able to absorb the mineralized nutrient phases.

In a further embodiment of the invention-based fermenter it has been arranged that said fermenter is downstream connected with a conventional biogas fermenter (so-called "repowering") in such a way that fermentation residues can be supplied from the conventional biogas fermenter by means of the inlet for the pumpable organic material.

Subsequently, this embodiment is called post fermenter. The term "conventional biogas fermenter" involves the state of the art biogas fermenters mentioned at the outset. These biogas fermenters are used to ferment renewable resources. They basically consist of a large stirring tank with a gas storage dome or a plug flow device (horizontal cylinder). They perform only an incomplete fermentation of the raw materials and, at the same time, have a continuous loss of methanogenic microorganisms. Moreover, they produce fermentation residues which are inadequately sanitized (short-circuit currents, see above) and which emit greenhouse gases (methane, nitrous oxide, $CO_2$, see above). Therefore, it is extremely advantageous to feed the fermentation residues of such a fermenter into the invention-based fermenter which, in this case, functions as a kind of post fermenter. In this way, an operator of a conventional biogas fermenter can effectively improve the efficiency and environmental friendliness of his plant with relatively low investments.

In this special embodiment it can be arranged that the biogas generated in the post fermenter is supplied to the gas storage system of the main plant.

In an especially preferred embodiment, it has been arranged that the recycling section is designed in such a way that the recovered specific lighter fractions of pumpable organic material can be re-supplied to the upstream biogas fermenter.

This involves the possibility of recovering and re-supplying to the fermentation process active biomass which, together with the fermented material, has been brought with state of the art equipment into fermenters and left there unutilized. In this way the yield can be considerably increased. Moreover by re-supplying the active biomass into the digester, the period for optimizing the plant during a first operation is considerably reduced. Basically, a biogas plant requires a certain time for optimization. This is due to the fact that first of all a stable flora of microorganisms has to be established in the plant. By means of the possibility to recover the microorganisms that are still present in the fermented material extracted from the digester, the period of building a stable and highly efficient micro flora is considerably reduced. As a result the maximum yield is achieved in a considerably shorter period of time.

The possibility of recovering the active biomass involves another advantage: The fermentation process is accelerated because it is possible to maintain in the digester a considerably higher density of active microorganisms. In this way, the flow capacity of the fermenter can be increased. This results in the fact that the invention-based fermenter can tolerate a considerably higher volume load.

It can also be arranged that the invention-based fermenter (alternatively or in addition to the embodiment previously mentioned) is downstream connected to a long-term hydrolysis reactor (with liquid preservation of substrates). Said long-term hydrolysis reactor is known under the term "LIGAVATOR" or "BETAVATOR." For example, such a reactor has a capacity of 1,500 m³. While the produce to be fermented is stored in such a reactor, an anaerobic fermentation process takes place (especially an ensiling process, i.e., lactic acid/acetic acid fermentation), which can result in short-chain metabolites (especially lactate, i.e., lactate acid and acetate, i.e., acetic acid), in a reduction of the pH value and a formation of $CO_2$. Especially the lactate acid and acetic acid can be metabolized in an excellent manner in the invention-based fermenter. The released $CO_2$ can also be supplied to the invention-based fermenter.

DRAWINGS AND EXAMPLES

The present invention is explained in more detail by means of the following figures and examples. It must be taken into consideration that the figures and examples are only of a descriptive nature. They do not serve the purpose to restrict the invention in nay way.

FIG. 1 shows a longitudinal exemplification of an embodiment of an invention-based fermenter 10 for the purpose of producing biogas from pumpable organic material. The fermenter has an inlet 11 for the pumpable organic material, a fixed bed reactor 12 for the pumpable organic material with at least one primary (rising) section 12a and a secondary (descending) section 12b, as well as at least one outlet 13 for the developing fermentation residues.

Furthermore, the fermenter comprises a sedimentation chamber 14 for the pumpable organic material which is located between the primary and secondary section 12a, 12b of the fixed bed reactor. It also comprises a recycling section 15 which is connected with the sedimentation chamber 14 and which is designed in such a way that specific lighter fractions of the pumpable organic material can be recovered and, if required, re-supplied into the rising (primary) section of the fixed bed reactor.

The fixed bed reactor 12 consists of a material which allows for a formation of basically longitudinal channels (analogous to parallel intestinal tubes, i.e., intestinal tracts).

Using a fixed bed reactor with these characteristics has many advantages. For example, a fixed bed reactor does not require its own stirring unit, which is used in stirred tank fermenters, because it is possible to direct the flow of material inside the reactor. The directed flow of material prevents especially the short-circuit currents which are unavoidable in stirred tank fermenters and which affect an effective sanitization of the fermenting material as well as an ideal fermentation. The provided fixed bed reactor supplies also a colonization substrate for methane-producing micro-organisms. In this way, contrary to a fermenter with a stirring unit, it is possible to achieve a layered formation of microbiocoenosis.

The recycling section 15 consists of a vertical tubular element and is located between the rising (primary) section 12a and the descending (secondary) section 12b of the fixed bed reactor.

The recycling section 15 is connected to the sedimentation chamber 14 by means of an overflow edge and is designed in such a way that specific lighter fractions 19 of the pumpable organic material can be recovered and re-supplied by means of an outlet 16 to the rising (primary) section of the fixed bed reactor. On the one hand, these specific lighter fractions involve specific lighter organic fractions, as, for example, volatile fatty acids. In conventional stirred tank fermenters these fractions form a floating layer and thus evade the fermentation process. Incidentally some of the volatile fatty acids easily transform into the gaseous phase and are thus permanently excluded from the fermentation process.

The specific lighter organic fractions contain also microorganisms (so-called "active biomass") which have been dissolved from the substrate of the fixed bed reactor and, without a recycling section, would be discharged with the fermentation residue from the fermenter. This involves also a continuous loss of micronutrients which have to be supplemented in conventional fermenters with a stirring unit. This, in turn, results in additional expenses and an additional introduction of heavy metal. Consequently, in conventional biogas fermenters the density of biogas-producing microorganisms is continuously reduced which results in the fact that these fermenters are basically operated with a microorganism density that is too low to achieve an ideal biogas yield. The invention-based recycling section allows these microorganisms to be recovered and re-supplied into the fermenter. As a result, the invention-based fermenter has a considerably higher density of microorganisms than a conventional fermenter and a considerably improved supply of micronutrients, which are circulated via the active biomass. Incidentally some of the volatile fatty acids easily transform into the gaseous phase and are thus permanently excluded from the fermentation process.

The specific lighter organic fractions contain also microorganisms (so-called "active biomass") which have been dissolved from the substrate of the fixed bed reactor and, without a recycling section, would be discharged with the fermentation residue from the fermenter. Consequently, in conventional biogas fermenters the density of biogas-producing microorganisms is continuously reduced which results in the fact that these fermenters are basically operated with a microorganism density that is too low to achieve an ideal biogas yield. The invention-based recycling section allows these microorganisms to be recovered and re-supplied into the fermenter. As a result, the invention-based fermenter has a considerably higher density of microorganisms than a conventional fermenter.

In addition, the fermenter comprises two relatively small stirring units 17a, 17b in the region of the inlet 11 and in the region of the sedimentation chamber 14. These stirring units are activated at regular intervals and, if required, prevent solid particles from settling. Compared with the stirring units known from conventional stirred tank fermenters, the stirring units shown have considerable smaller dimensions and lower power consumption.

Moreover, the fermenter has a pump 18 to pump the fermenting material through the fixed bed reactor. Compared with the stirring units known from conventional stirred tank fermenters, also this pump has considerably lower power consumption. It can involve particularly a double piston pump. In addition, FIG. 1 shows a gas dispensing device 20 for extracting the generated biogas.

The solid arrows show the direction through the fermenter of the flow of material. The dashed arrows shoe the direction of the generating biogas.

FIG. 1 shows also clearly that the invention-based fermenter requires considerably less surface area than a conventional stirred tank fermenter, which requires a very large surface area because of the large digester capacity. In a preferred embodiment, the invention-based fermenter has a base area of merely 29 m$^2$ and can thus be integrated easily in available farming sites.

Figure 2A:
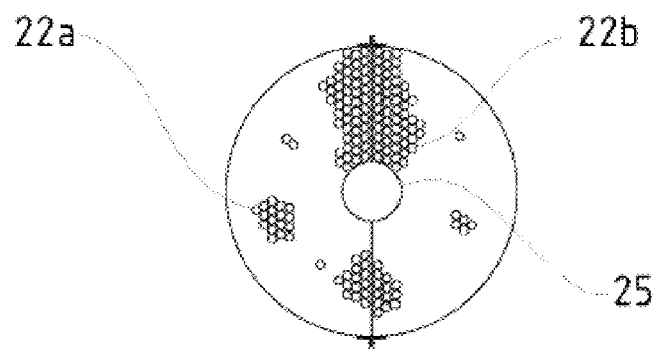
FIG. 2A shows a cross section of the invention-based fermenter along the lines A-A' shown in FIG. 1.
Figure 2B:
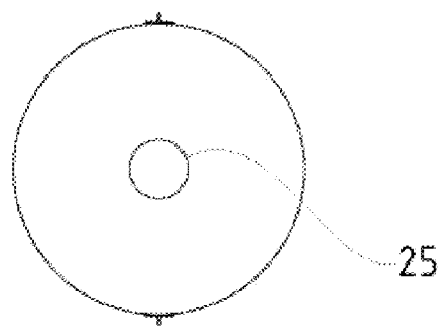
FIG. 2B shows a cross section of the invention-based fermenter along the lines B-B' shown in FIG. 1.
Figure 3A:
FIG. 3A shows an example of a plastic drain pipe that can be used as a material for the solid-body reactor.

FIG. 2 shows two cross sections of the invention-based fermenter along the lines A-A' (FIG. 2A) or B-B' (FIG. 2B). A top view of FIG. 2a shows the rising (primary) section 22a and the descending (secondary) section 22b of the fixed bed reactor, as well as the recycling section 15. FIG. 2b shows a top view of the overflow edge with the upper edge of the recycling section. FIG. 3a shows an example of a plastic pipe 31 which is preferably used as material for the solid-body reactor because it allows for a formation of basically longitudinal channels. This pipe has an enlarged surface on its outer surface as well as its inner surface and provides a large surface for microbial colonization. The plastic pipe involves a pipe that has characteristics similar to the known flexible drain pipes used in underground construction with a diameter of between 50 and 400 mm. It is especially preferred to use this type of drain pipe because it is light and cost-effective. Preferably arrangements are made that many such pipes are suspended in the fermenter, thus forming the fixed bed reactor. For this purpose it can be arranged that the fermenter comprises in its upper and lower region a respective suspension device in order to suspend the plastic pipes mentioned.

Other materials to form the fixed bed reactor comprise, for example, vertical pipes or honeycomb-shaped hollow bodies consisting of ceramics, clay, earthenware, wood, metal or plastic material, or vertical rods, ropes, cords or strings.

Figure 3B:
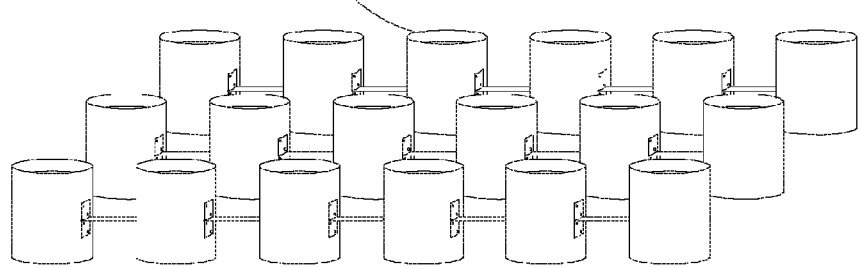
FIG. 3B shows an example of a retaining device for the plastic drain pipes.

FIG. 3b shows an example of a retaining device 33 for these plastic pipes which is attached to the upper and lower end of the fixed bed reactor, respectively, and which fixes the best possible distance of the pipes to one another and does not restrict the pipe passages, but rather prevents such restrictions. The retaining device consists of stainless steel pipe sections ("sleeves") which are arranged in a surface area and which are welded or otherwise connected to one another with angle brackets. The ends of the plastic pipes fit perfectly into the retaining device.

Figure 4:
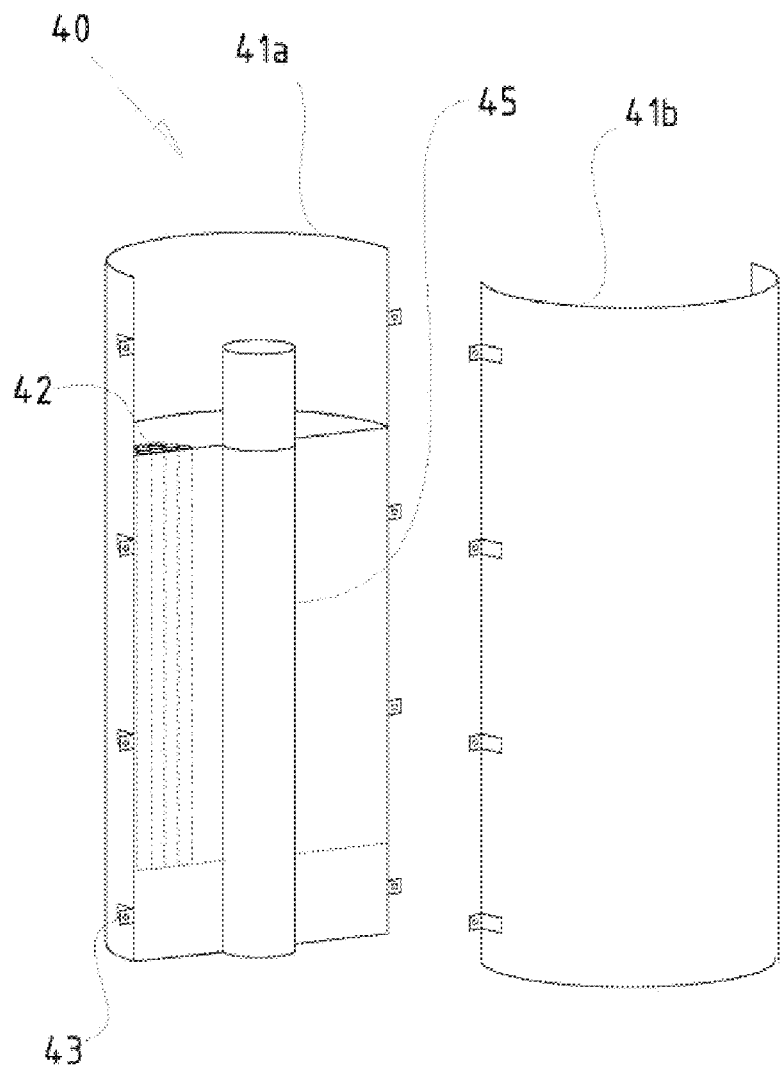
FIG. 4 shows an exploded view of a portion of the invention-based fermenter including two cylinder halves.

FIG. 4 shows an exploded view of a portion 40 of the invention-based fermenter, consisting of the two cylinder halves 41a and 41b. FIG. 4 shows a top view of the rising (primary) section 42 of the fixed bed reactor. The descending section in FIG. 4 is covered by the wall of the segment 41b and is therefore not visible. The segments are screwed together on site by means of mounting brackets 43. Ideally one of the segments (here 41a) includes already the recycling section 45, which also facilitates production and installation and thus reduces costs.

Figure 5:
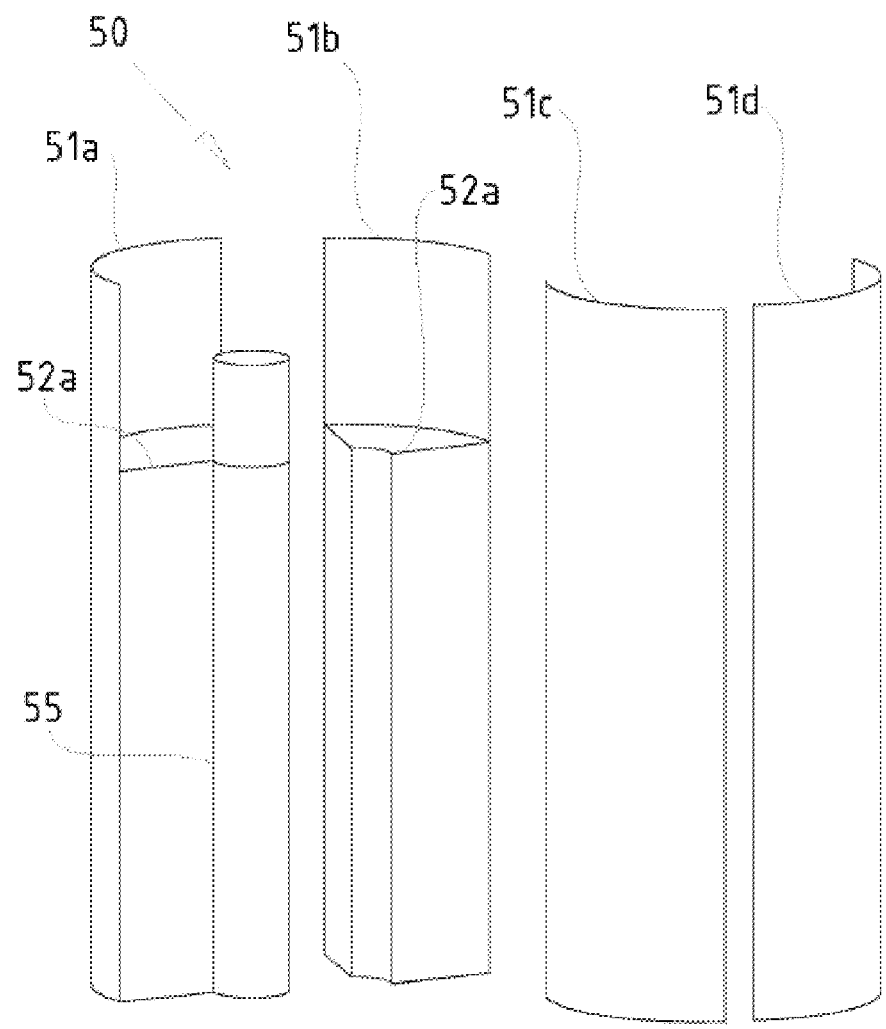
FIG. 5 shows an exploded view of a 4-segment invention-based fermenter.

FIG. 5 also shows an exploded view of a portion 50 of an invention-based fermenter. In contrast to the fermenter shown in FIG. 4, this fermenter consists of 4 segments 51a-51d. Consequently, the rising (primary) section of the fixed bed reactor consists of 2 segments 52a and 52b. The descending section in FIG. 5 is covered by the wall of the segments 51c and 51d and is therefore not visible. FIG. 5 also shows the recycling section 55.

Figure 6:
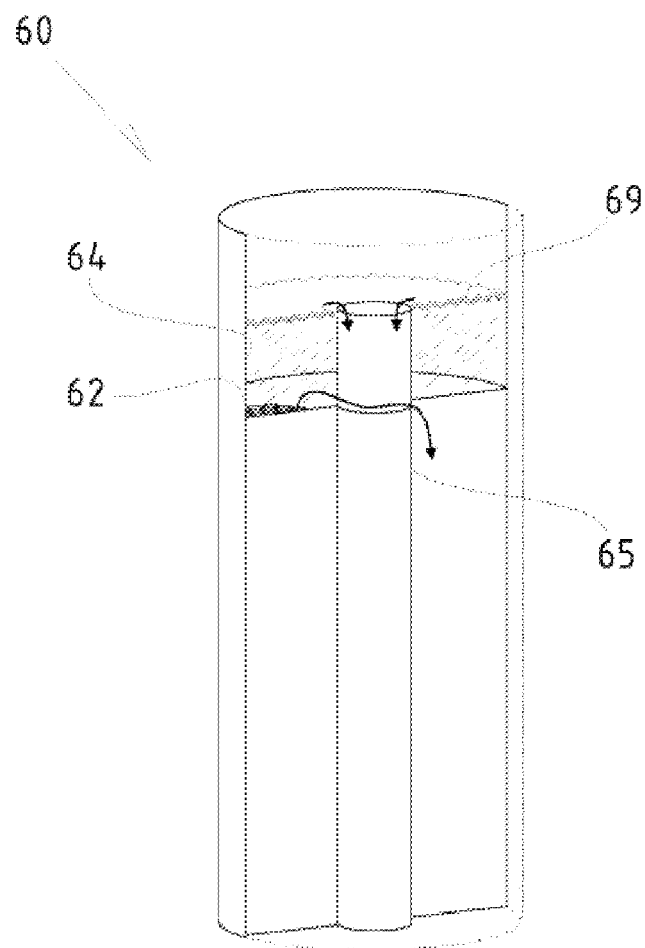
FIG. 6 shows a portion of an invention-based fermenter in a sectional cut indicating the flow patterns of the fermenting material.

FIG. 6 also shows a portion 60 of an invention-based fermenter in a sectional cut with the flow patterns of the fermenting material. The fermenting material is transferred from the rising (primary) section 62 of the fixed bed reactor to the sedimentation chamber 64. There specific lighter fractions 69 settle on the top and are transferred to the recycling section 65 by means of an overflow edge. However, the specific heavier fractions (for example, non-gaseous dead biomass) are transferred to the descending (secondary) section (not shown) of the fixed bed reactor.

Figure 7A:
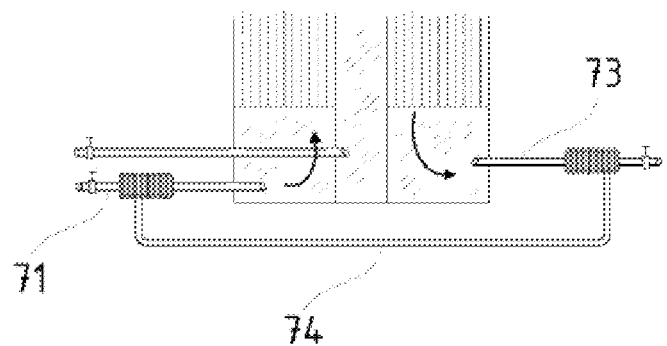
FIG. 7a shows a heat exchanger which is located in the region of the outlet.

FIG. 7 shows different complementary embodiments of the invention-based fermenter. For example, FIG. 7a shows a heat exchanger 74 which is located in the region of the outlet 73. The fresh organic material to be fermented can be heated by means of this heat exchanger. For this purpose, the heat exchanger is connected to the outlet 71.

This considerably facilitates the mesophilic or thermophilic conditions in the fermenter. At the same time it reduces the energy consumption required. In an ideal case, the intrinsic reaction heat developing during the fermentation process is sufficient to adjust the above-mentioned conditions. Consequently, no additional heat supply from the outside is required.

Figure 7B:
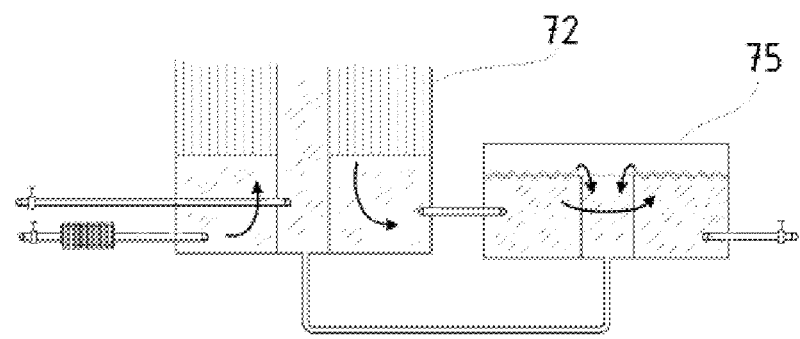
FIG. 7b shows an additional recycling section which is located behind the descending (secondary) section of the fixed bed reactor.

FIG. 7b shows an additional recycling section 75 which is located behind the descending (secondary) section of the fixed bed reactor 72. In this way, the recovery of said substrates and microorganisms is further improved.

Figure 8:
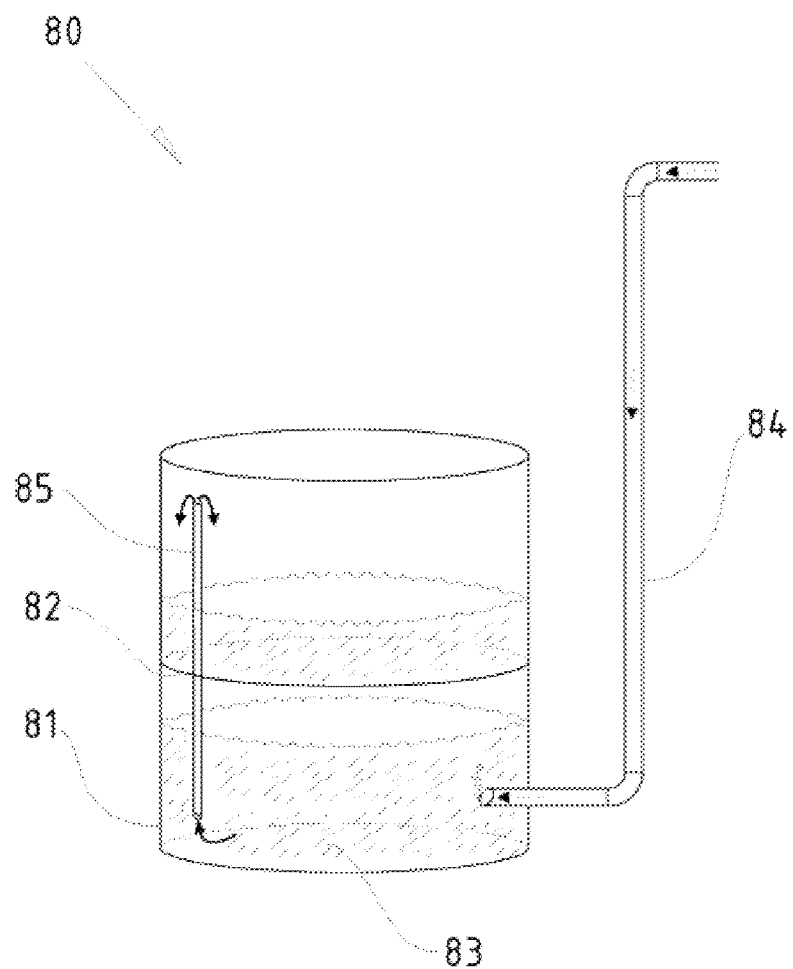
FIG. 8 shows a hydrostatic gas storage system.

FIG. 8 shows a hydrostatic gas storage system 80, consisting of a container 81 with an intermediate bottom 82. The bottom part of the container is filled with buffer fluid 83. The gas storage system is connected to a gas dispensing device 84 of a fermenter that is not shown. During the process of flowing into the lower part of the container, the supplied gas displaces the liquid (in particular water) with gravity (and thus against the formation of hydrostatic pressure or a water column). The water rises through a riser tube 85 into the upper part of the container. If, for example, the gas storage system is constructed in a way that, when displacing the liquid available in the system, the gas inflow forms a maximum water column of 2,000 mm, it corresponds to a hydrostatic pressure of 200 mbar. At the same time, the pressure of the stored gas is maintained at a level corresponding to the hydrostatic pressure and can be supplied to the gas engine of the BHKW without using its own gas pressure blower. For this purpose it is essential that the biogas generating microorganisms are able to continue to produce biogas even against strong pressure gradients. Consequently, the biogas synthesis is not affected by the described accumulating pressure gradient of 200 mbar, which could possible continue all the way into the fermenter.

Figure 9:
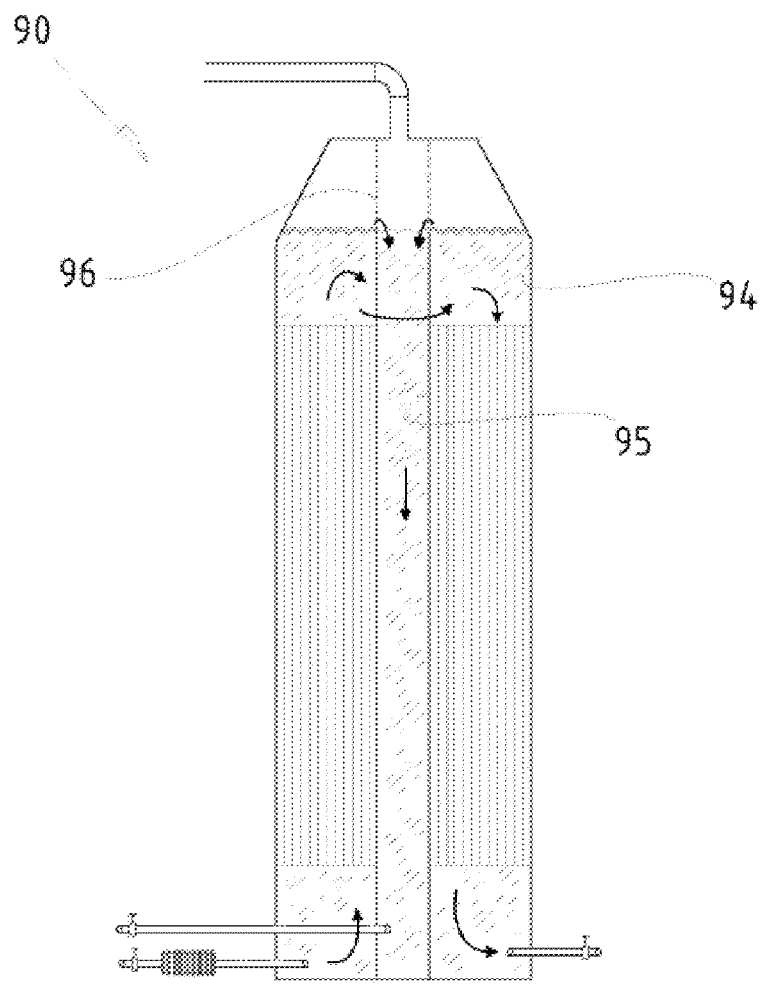
FIG. 9 shows a further embodiment of an invention-based fermenter in which the sedimentation chamber is connected to the recycling section through peripheral boreholes or screening devices.

FIG. 9 shows a further embodiment of an invention-based fermenter 90 which corresponds in most aspects the embodiment shown in FIG. 1. However, in contrast to the embodiment shown in FIG. 1, the sedimentation chamber 95 is connected to the recycling section 94 through peripheral boreholes 96 or screening devices, and not by means of an overflow edge.

Figure 10:
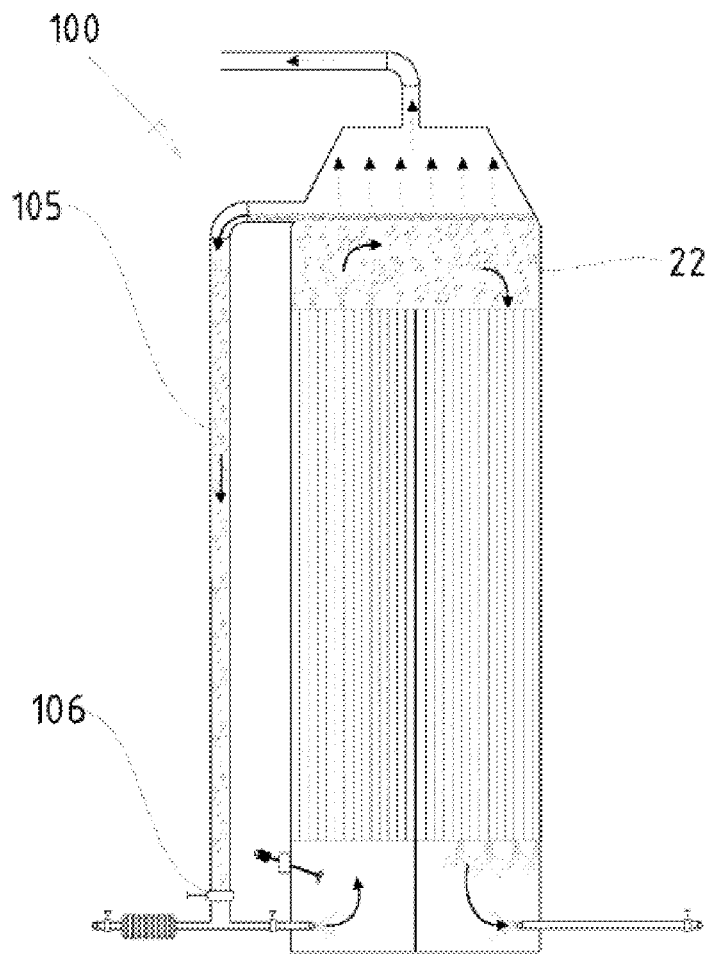
FIG. 10 shows a further embodiment of an invention-based fermenter in which the sedimentation chamber is located externally.

FIG. 10 shows a further embodiment of an invention-based fermenter 100 which also corresponds in most aspects the embodiment shown in FIG. 1. However, in contrast to the embodiment shown in FIG. 1, the sedimentation chamber 105 is located externally, being connected to the recycling section 104. The amount of the recirculation flow can be regulated by means of a valve 106. In this design, it is easy to separate the sedimentation chamber from the fermenter for maintenance purposes.

Figure 11:
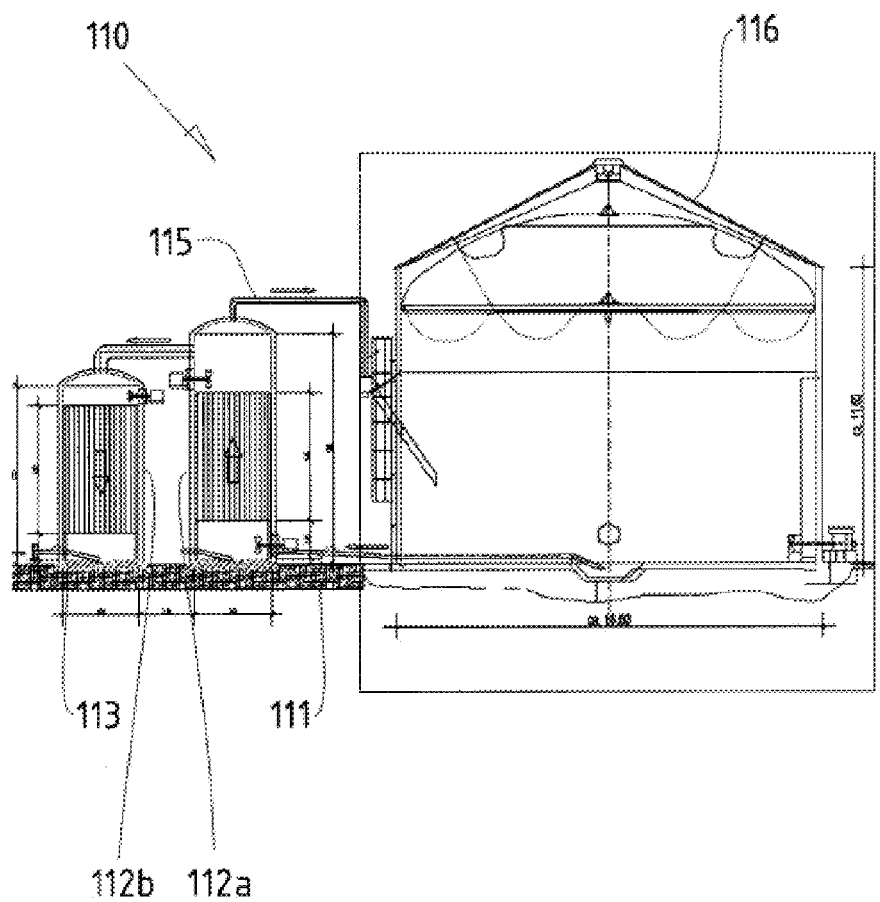
FIG. 11 shows a further embodiment of the invention-based fermenter having a primary (rising) section and a secondary (descending) section which are separated structurally from one another and an optional conventional biogas fermenter connected downstream of the invention-based fermenter.

FIG. 11 shows a further embodiment of the invention-based fermenter including the inlet 111, a fixed bed reactor 112 for the pumpable organic material with a primary (rising) section 112a and a secondary (descending) section 112b, which are separated structurally from one another (so-called partial fermenters), as well as an outlet 113. To save expenses, the sections 112a and 112b can be made from a used liquefied gas tank or gas tank which has been cut through the center. In the head piece of the partial fermenter, a sedimentation chamber 115 has been provided by means of which recovered specific lighter fractions of pumpable material is re-supplied to the upstream biogas fermenter 116. The material is transported by means of gas pressure which is especially generated in the rising section of the fermenter.

FIG. 11 shows also an optionally provided conventional biogas fermenter 116 which is downstream connected with the invention-based 110 fermenter and which functions toward the invention-based fermenter as a post fermenter (so-called "repowering") in such a way that fermentation residues can be supplied by means of the inlet.

In a further embodiment of the invention-based fermenter it has been arranged that said fermenter is downstream connected with a conventional biogas fermenter (so-called "repowering") in such a way that fermentation residues can be supplied from the conventional biogas fermenter by means of the inlet for the pumpable organic material.

Basically, the biogas fermenter 116 consists of a large stirring tank with a gas storage dome. It performs only an incomplete fermentation of the raw materials (i.e., high of remaining gas potential of the fermentation residue) and, at the same time, it has a continuous loss of methanogenic microorganisms. Moreover, it produces fermentation residues which are inadequately sanitized and mineralized (fermented) (short-circuit currents, see above) and which, above all, emit greenhouse gases (methane, nitrous oxide, $CO_2$, see above). Therefore, it is extremely advantageous to feed the fermentation residues of such a fermenter 116 into the invention-based fermenter 112. In this way, an operator of a conventional biogas fermenter can effectively improve the efficiency and environmental friendliness of his plant with relatively low investments.

In the process, the biogas produced in the fermenter 112 is supplied to the gas storage system of the biogas fermenter 116. In an especially preferred embodiment it has been arranged that the sedimentation chamber 115 is designed in such a way that the recovered specific lighter fractions of pumpable organic material can be re-supplied to the upstream biogas fermenter 116.

The invention claimed is:

1. A fermenter for generating biogas from pumpable organic material with a low content of organic dry matter (oTS), comprising
    a) at least one inlet for the pumpable organic material,
    b) at least one fixed bed reactor for the pumpable organic material with at least one primary and one secondary section,
    c) at least one outlet for the remaining fermentation residue,
    d) at least one recycling section for the pumpable organic material, the at least one recycling section being located between the primary and secondary sections of the fixed bed reactor, and
    e) at least one sedimentation chamber connected to the at least one recycling section, the at least one sedimentation chamber configured such that specific lighter fractions of the pumpable organic material are recovered and resupplied to the primary section of the fixed bed reactor.

2. A fermenter according to claim 1, characterized in that the primary section of the fixed bed reactor is a rising section and the secondary section of the fixed bed reactor is a descending section.

3. A fermenter according to claim 1, characterized in that the fixed bed reactor is formed of a material which provides a large colonization surface for microorganisms.

4. A fermenter according to claim 1, characterized in that the fixed bed reactor is formed of a material that allows for the formation of basically longitudinal channels.

5. A fermenter according to claim 1, characterized in that the at least one sedimentation chamber includes a vertical tubular element which, optionally, comprises several parts.

6. A fermenter according to claim 1, characterized in that the at least one sedimentation chamber is located between the primary section and the secondary section of the fixed bed reactor.

7. A fermenter according to claim 1, further comprising a second sedimentation chamber located downstream from the secondary section of the fixed bed reactor.

8. A fermenter according to claim 1, characterized in that the fermenter is in the form of a vertical cylinder.

9. A fermenter according to claim 1, characterized in that the fermenter includes several segments which can be produced in a manufacturing company and assembled to a fermenter on site.

10. A fermenter according to claim 1, characterized in that the fermenter has a gas collection device which is located at least partially above the fixed bed reactor.

11. A fermenter according to claim 10, characterized in that the gas collection device comprises a conical or frustoconical, paraboloid or hemispherical dome.

12. A fermenter according to claim 1, further comprising a hydrostatic gas storage system.

13. A fermenter according to claim 1, further comprising a heat exchanger in the region of the outlet of the fermenter, wherein said heat exchanger is configured to pre-heat fresh organic material prior to fermentation.

14. A fermenter according to claim 1, further comprising a temperature control device for the organic material to be fermented that is set in such a way that the temperature of the fermenting material, which is brought into the digester through the inlet, can be adjusted only by heating the organic material to be fermented.

15. A fermenter according to claim 1, characterized in that the fermenter is downstream connected with a conventional biogas fermenter in such a way that fermentation residues can be supplied from the conventional biogas fermenter by means of the inlet for the pumpable organic material.

16. A fermenter according to claim 15, characterized in that the sedimentation chamber is designed in such a way that the recovered specific lighter fractions of pumpable organic material can be re-supplied to the upstream biogas fermenter.

17. A fermenter according to claim 1, characterized in that it is downstream connected to a long-term hydrolysis reactor.

18. A method for generating biogas from pumpable organic material with a low content of organic dry substance (oTS) in a fermenter according to claim 1, which comprises the following steps:
a) inserting the pumpable organic material through an inlet in the fermenter,
b) producing and maintaining an anaerobic environment, a pH value of at least 7 and temperature in a mesophilic to thermophilic range,
c) producing a flow of material of pumpable organic material through the fixed bed reactor as well as the sedimentation chamber of the fermenter,
d) recovering in the recycling section the specific lighter fractions of the pumpable organic material,
e) if possible, re-supplying the recovered material to the fermenter,
f) collecting the generated gas and extracting the fermented fermentation residue continuously and in batches.

19. A method according to claim 18, characterized in that the recovered material is pre-incubated with fresh material to be fermented before the fresh material is brought into the fermenter.

20. A method according to claim 18, characterized in that for the purpose of full utilization, more biomass, for example from renewable resources, especially from energy crops, is supplied to the organic material to be fermented.

21. A method according to claim 18, characterized in that the process conditions are adjusted in such a way that the formation of propionic acid is reduced or that the reduction of propionic acid is promoted.

\* \* \* \* \*